US006263235B1

(12) United States Patent
Kaiser et al.

(10) Patent No.: US 6,263,235 B1
(45) Date of Patent: Jul. 17, 2001

(54) ELECTROCARDIOGRAM ARRANGEMENT

(75) Inventors: Willi Kaiser, Emmendingen; Martin Findeis, Freiburg, both of (DE)

(73) Assignee: GE Marquette Hellige GmbH, Freiburg i. Br. (DE)

( * ) Notice: Subject to any disclaimer, the term of this patent is extended or adjusted under 35 U.S.C. 154(b) by 0 days.

(21) Appl. No.: 09/421,683

(22) Filed: Oct. 20, 1999

(30) Foreign Application Priority Data

Oct. 23, 1998 (DE) .............................................. 198 49 034

(51) Int. Cl.7 .................................................. A61B 5/0402
(52) U.S. Cl. ............................................................ 600/509
(58) Field of Search ..................................... 600/509, 512, 600/521, 522, 523

(56) References Cited

U.S. PATENT DOCUMENTS 4,987,901  1/1991  Kunig .................................... 128/696

OTHER PUBLICATIONS

"Arrhythmia Analysis by the Louvain VCG Program," by Christian R. Brohet, Christiane Derwael–Barchy, Robert Fesler and Lucien A. Brasseur, Computers in Cardiology, 1981, pp. 47–51.

"Multilead ECG Analysis," by Jan A. Kors, Jan L. Talmon and Jan H. Van Bemmel, Computers and Biobedical Research 19, 1986, pp. 28–46.

*Primary Examiner*—Scott M. Getzow
(74) *Attorney, Agent, or Firm*—Michael Best & Friedrich LLP

(57) ABSTRACT

The invention relates to an electrocardiogram arrangement having a plurality of lead channels, in which at least two lead channels are assigned an evaluation unit (1, 2, . . . ) which evaluates the ECG quality, classifies the results and locates the QRS complexes. For the QRS complex location, a central logic unit (14) selects that lead channel which has the highest ECG quality as the dominant lead channel. When special events occur in the dominant lead channel, other lead channels are accessed as appropriate.

30 Claims, 1 Drawing Sheet

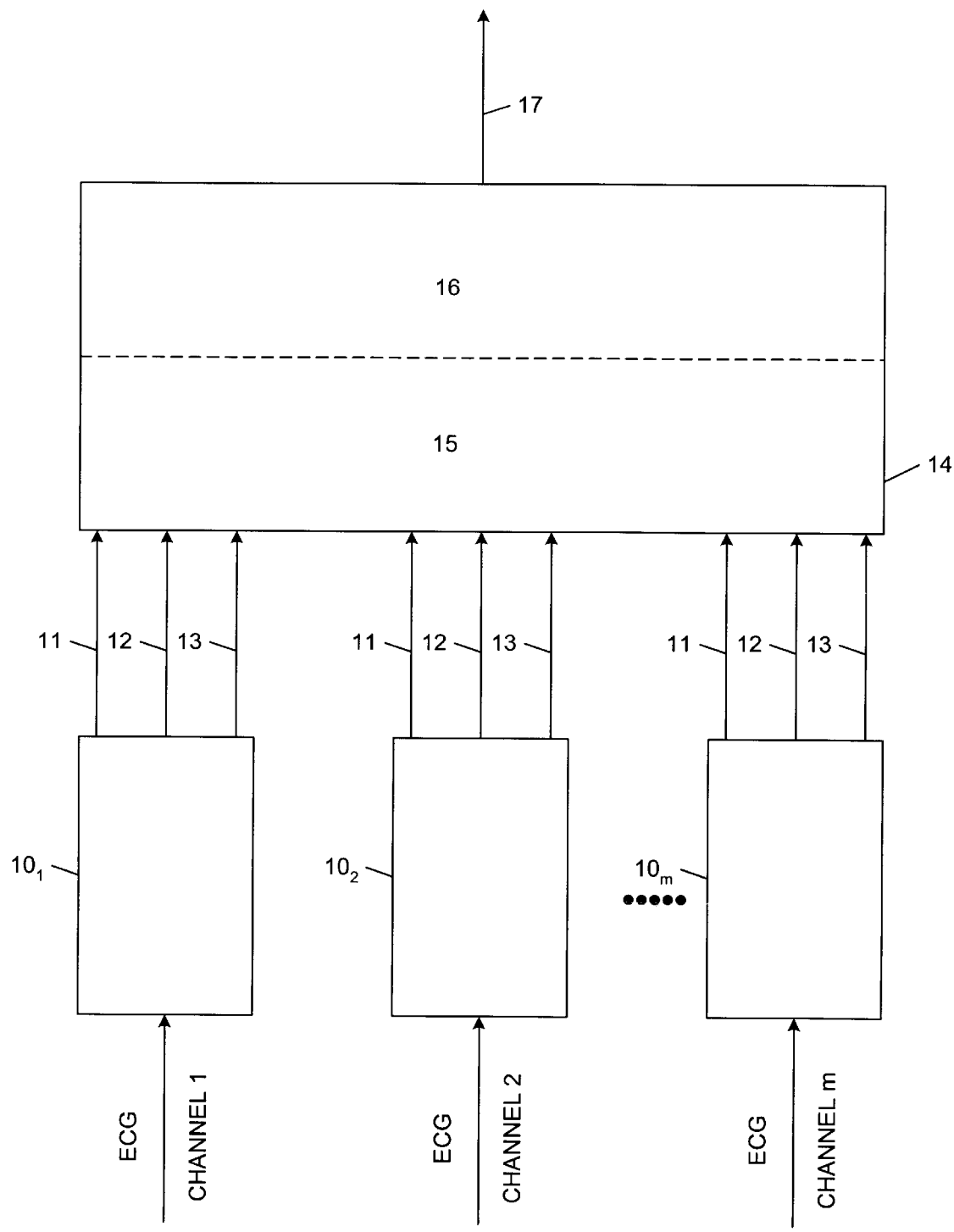

ELECTROCARDIOGRAM ARRANGEMENT

BACKGROUND OF THE INVENTION

The present invention relates to an electrocardiogram (ECG) arrangement having m (m≧2) lead channels for locating QRS complexes in an electrocardiogram and having a central logic unit.

As is known, in ECG examinations, it is becoming evermore frequent to use electrocardiogram arrangements having a plurality of lead channels which are usually fitted to the arms and legs (limb lead) and to the chest (chest lead). In the main, electrocardiogram arrangements which have twelve lead channels are available. There are, however, also electrocardiogram arrangements in which more or fewer than twelve lead channels are employed.

By way of example, for measuring heart rate or for analyzing arrhythmia, the redundancy involved with having multiple lead channels provides advantages when this redundancy is used to reduce or eliminate the effect of noise or artifacts in the result obtained using the electrocardiogram arrangement.

Previous electrocardiogram arrangements have exploited the multiple lead-channel redundancy and have collated the individual lead-channel signals by taking their first mathematical derivative. The individual mathematical derivatives are squared and then summed over all the lead channels. The square root of the result obtained in this way is then taken. The signal obtained in this way has the advantage that, compared with the individual original signals, the ratio of the useful signal component to the noise signal component is improved, which in the final analysis means that the QRS complexes can be located better.

Instead of squaring and taking the square root, sometimes only the magnitude of the signals given by the first mathematical derivative is calculated, this being followed by summing the magnitudes obtained for the individual lead channels.

In any event, with both electrocardiogram arrangements, the final result is a one-channel signal which is subjected to evaluation in relation to the QRS complexes.

The conventional electrocardiogram arrangements constructed in this way give reliable results if the level of noise is approximately the same in all the lead channels. However, if some of the lead channels have substantially stronger interference than other lead channels, which is often the case, for example, when recording a stress test electrocardiogram, it is expedient to exclude the signals from the very noisy lead channels from any subsequent processing.

SUMMARY OF THE INVENTION

To that end, there are already electrocardiogram arrangements which, although they are constructed in the manner indicated above, they only use signals from lead channels which are empirically found to have relatively few artifacts and are approximately orthogonal to one another. This is because the orthogonality of the lead-channel signals ensures that the normal QRS complexes or ventricular extrasystoles are well represented in at least one of the signals. The disadvantage with a procedure of this type is, however, that because of the requirement of evaluating mutually orthogonal signals, lead-channel signals which have stronger interference than other signals also have to be used aid, in the final analysis, an electrocardiogram arrangement constructed in this way only gives good results under certain circumstances.

It is known that, in a stress test electrocardiogram, most interference occurs in the heavy load phase. However, the heavy load phase is actually one of the most important phases of a stress test. For example, it is during this phase that the doctor decides, amongst other things, whether or not the examination should be stopped.

In order to decide whether or not the heavy load phase should be stopped, amongst other things the heart rate, the ST segment of the electrocardiogram and arrhythmia results are employed.

It is therefore very important to be able to calculate correctly the data relevant to this decision actually in the heavy load phase, in spite of the greater incidence of interference. One prerequisite for such correct calculation of the data is, however, accurate location of the QRS complexes.

The object of the present invention is therefore to provide an electrocardiogram arrangement which allows accurate location of QRS complexes even during heavy load phases.

This object is achieved according to the invention, with an electrocardiogram arrangement of the type mentioned at the start, in the following way:

n (n≦m) independent evaluation units are provided in the plurality of lead channels, each lead channel being respectively assigned at most one evaluation unit which locates the QRS complexes, classifies the events and assesses the ECG quality, a comparator, in the central logic unit connected to the individual evaluation units, which compares with one another the ECG qualities obtained by the ECG quality assessments in the individual lead channels and identifies the lead channel obtaining the highest ECG quality as the dominant lead channel, and a test unit, in the central logic unit, which tests the results of the event classification of the dominant lead channel and, when special events occur in the dominant lead channel, accesses other lead channels in order to correct the results of the QRS complex location and the event classification of the dominant lead channel on that basis.

BRIEF DESCRIPTION OF THE DRAWINGS

FIG. 1 is a schematic view of a processor embodying the invention.

DETAILED DESCRIPTION

In this regard, the electrocardiogram arrangement according to the invention firstly uses the fact that, during a heavy load phase, the signals of virtually all the lead channels are noisy. It is indeed often the case that only the signals from one or two lead channels are useable, while the signals from all the other lead channels vitiate the results since the interference in them is too strong.

In the electrocardiogram arrangement according to the invention, the QRS complexes in the various lead channels are evaluated and located separately. This means that, in contrast to the prior art, the individual ECG curves from the various lead channels are not combined to form one signal. Instead, quality assessments are made in each individual lead channel and, in order to do this, quality features are calculated separately. The instance of the QRS complexes located in this way, and their event classification, are taken from the lead channel with the highest ECG quality, referred to as the dominant lead channel, and are for example used to calculate the heart rate.

In the event of special results in the electrocardiogram of the dominant lead channel, for example a pause, a superventricular extrasystole or a fusion beat, the QRS complex features from other lead channels are accessed. If, for example, a pause occurs in the dominant lead channel, then the corresponding features are taker from a different lead channel, if a QRS complex, for example a ventricular extrasystole, has been located at this point.

Examples of the features for determining the ECG quality include:

the amplitude of the QRS complexes, a noise level value for high-frequency interference, for example caused by muscle tremors, a noise level value for medium-frequency interference, for example caused by motion of the electrodes relative to the patient's body, and the electrode condition, for example electrodes having fallen off.

The following features, in particular, are thus essential to the electrocardiogram arrangement according to the invention for reliable location of QRS complexes in an electrocardiogram:

Two or more independent evaluation units, which are equivalent to one another, are used for location and event classification of QRS complexes and for ECG quality evaluation in each individual lead channel.

On the basis of the ECG quality of the individual lead channels, a central logic unit takes the results of the QRS location and the event classification from the "best" lead channel.

The central logic unit tests the event classification of the "best" lead channel for events, for example pauses, superventricular extrasystoles or fusion beats, accesses the results from the other lead channels and, on the basis of their results, corrects the results of the event classification and the QRS location of the "best", or dominant, lead channel.

The specific selection of the lead channels having the signals with the least interference, which is carried out in this way, improves the QRS complex location in comparison with conventional arrangements. Consequently, the quality of the algorithms based on this, such as heart rate calculation, and even beat averaging for ST measurement, is also improved.

The invention will be explained in more detail below with the aid of the drawing, the single figure of which schematically represents a block diagram of the electrocardiogram arrangement according to the invention.

In the electrocardiogram arrangement according to the invention, ECG lead channels 1, 2, . . . , m are fed to evaluation units $10_1, 10_2, \ldots, 10_m$, although each ECG lead channel need not necessarily have such an evaluation unit $10_1, 10_2, \ldots, 10_m$. However, no more than one evaluation unit is provided in each ECG lead channel, so that the number of evaluation units $10_1, 10_2, \ldots, 10_m$ corresponds at most to the number of ECG lead channels. QRS complex location, event classification and ECG quality assessment are carried out in each of the ECG evaluation units, this being done in a conventional way. The results of this QRS complex location, this event classification and this ECG quality assessment are all fed to a central logic unit 14, this being indicated by arrows 11, 12 and 13, respectively, which in particular has a comparator 15 and a test unit 16. The comparator 15 compares with one another the ECG qualities obtained using the individual evaluation units $10_1, 10_2, \ldots, 10_m$ for the lead channels, and identifies the lead channel obtaining the highest ECG quality. The QRS complex location (see arrow 11) of the lead channel which has the highest ECG quality is then selected by the comparator 15 for it to be processed further. The test unit 16 tests the event classification of the dominant lead channel and, when special events occur, for example pauses, superventricular extrasystoles and fusion beats, accesses other lead channels and, on the basis of this access, corrects the event classification and the result of the QRS complex location of the dominant lead channel.

Said further processing may, for example, involve calculating the heart rate. Other processing operations are, however, also possible.

Finally, the QRS location results and the event classification results (see arrow 17) are output by the central logic unit 14.

What is claimed is:

1. Electrocardiogram (ECG) arrangement having m (m≧2) lead channels (1, 2, . . . , m) for locating QRS complexes in an electrocardiogram and having a central logic unit (14), wherein n (n≦m) independent evaluation units ($10_1, 10_2, \ldots$) are provided in the plurality of lead channels (1, 2, . . . , m), each lead channel being respectively assigned at most one evaluation unit ($10_1, 10_2, \ldots$) which locates the QRS complexes (11), classifies the events (12) and assesses the ECG quality (13), a comparator (15), in the central logic unit (14) connected to the individual evaluation units (1, 2, . . . ), which compares the ECG qualities obtained by the ECG quality assessments in the individual lead channels (1, 2, . . . ) and identifies the lead channel obtaining the highest ECG quality as the dominant lead channel, and a test unit (16), in the central logic unit (14), which tests the results of the event classification (12) of the dominant lead channel and, when special events occur in the dominant lead channel, accesses other lead channels in order to correct the results of the qrs complex location (11) and the event classification (12) of the dominant lead channel.

2. Arrangement as claimed in claim 1, wherein special events are pauses, superventricular extrasystoles and fusion beats.

3. Arrangement as claimed in claim 2, wherein a heart rate is calculated in subsequent processing.

4. Arrangement as claimed in claim 1, wherein a heart rate is calculated in subsequent processing.

5. A medical device comprising a processor operable to receive a plurality of electrocardiogram (ECG) lead channels from a patient, the number of ECG lead channels being represented by the number (m) where (m) is equal to or greater than two, the processor including:

a plurality of evaluation units, the number of evaluation units being represented by the number (n) where (n) is less than or equal to (m), each evaluation unit being operable to receive one ECG lead channel, to assess the quality of the received ECG lead channel, and to produce an ECG quality assessment of the ECG lead channel; and a comparator being operable to identify and select a best ECG lead channel based on the ECG quality assessments resulting from the plurality of evaluation units.

6. A medical device as set forth in claim 5 wherein each ECG lead channel assessed includes at least one QRS complex, and wherein each evaluation unit is further operable to locate the at least one QRS complex the received of each ECG lead channel.

7. A medical device as set forth in claim 5 wherein each evaluation unit is further operable to determine if the received ECG channel has an event and to classify each event determined.

8. A medical device as set forth in claim 7 wherein the processor further includes a test unit being operable to test the events of the best lead for special events.

9. A medical device as set forth in claim 8 wherein the special events tested for include pauses.

10. A medical device as set forth in claim 8 wherein the special events tested for include superventricular extrasystoles.

11. A medical device as set forth in claim 8 wherein the special events tested for include fusion beats.

12. A medical device as set forth in claim 8 wherein each ECG lead channel assessed includes at least one QRS complex, and wherein each evaluation unit is further operable to locate the at least one QRS complex the received of each ECG lead channel.

13. A medical device as set forth in claim 12 wherein the test unit is further operable to correct the event classification and the QRS complex location of the best ECG channel lead with non-best ECG channel leads when the special event occurs.

14. A method of selecting an electrocardiogram (ECG) lead channel from a plurality of ECG lead channels, the number of ECG lead channels being represented by the number (m) where (m) is equal to or greater than two, the method comprising the acts of:
   assessing the quality of at least two of the ECG lead channels, the act of assessing including generating at least one ECG quality assessment for each ECG lead channel assessed;
   identifying the ECG lead channel having the highest quality assessment;
   selecting the identified ECG lead channel having the highest quality assessment, the selected ECG lead channel being a best ECG lead channel.

15. A method as set forth in claim 14 wherein the number of assessed ECG channels is represented by the number (n), and wherein (n) is less than or equal to (m).

16. A method as set forth in claim 14 wherein the act of assessing the quality of at least two of the ECG lead channels includes the act of assessing features of each ECG lead channel assessed.

17. A method as set forth in claim 16 wherein each ECG lead channel assessed has at least one QRS complex, and wherein the act of assessing features of each ECG lead channel assessed includes the act of determining the amplitude of the at least one QRS complex of each ECG lead assessed.

18. A method as set forth in claim 16 wherein the act of assessing features of each ECG lead channel assessed includes the act of determining a high-frequency-interference noise level value for each ECG lead channel assessed.

19. A method as set forth in claim 16 wherein the act of assessing features of each ECG lead channel assessed includes the act of determining a medium-frequency-interference noise level value for each ECG lead channel assessed.

20. A method as set forth in claim 16 wherein the act of assessing features of each ECG lead channel assessed includes the act of determining an electrode condition for each ECG lead channel assessed.

21. A method as set forth in claim 14 wherein each ECG lead channel assessed includes at least one QRS complex, and wherein the method further comprises the act of locating the QRS complexes of each ECG lead channel assessed.

22. A method as set forth in claim 21 wherein the act of testing the classified events of the best ECG lead channel for special events includes the act of testing the classified events of the best ECG lead channel for superventricular extrasystoles.

23. A method as set forth in claim 14 and the method further comprises the acts of:
   determining if an ECG lead channel assessed includes an event; and
   classifying each event determined.

24. A method as set forth in claim 23 and further comprising the act of testing the classified events of the best ECG lead channel for special events.

25. A method as set forth in claim 24 wherein the act of testing the classified events of the best ECG lead channel for special events includes the act of testing the classified events of the best ECG lead channel for pauses.

26. A method as set forth in claim 24 wherein the act of testing the classified events of the best ECG lead channel for special events includes the act of testing the classified events of the best ECG lead channel for fusion beats.

27. A method as set forth in claim 24 wherein the act of assessing features of each ECG lead channel assessed includes the act of determining a medium-frequency-interference noise level value for each ECG lead channel assessed.

28. A method as set forth in claim 27 and further comprising the acts of:
   testing the classified events of at least one non-best ECG lead channel; and
   correcting the event classification and the QRS complex location of the dominant ECG lead channel.

29. A method as set forth in claim 27 and further comprising the act of outputting the QRS location results and the event classification results of the best ECG lead channel.

30. A method as set forth in claim 14 and further comprising the act of calculating the heat rate of the best ECG lead channel.

* * * * *

UNITED STATES PATENT AND TRADEMARK OFFICE
CERTIFICATE OF CORRECTION

PATENT NO.    : 6,263,235 B1
DATED         : July 17, 2001
INVENTOR(S)   : Willi Kaiser et al.

It is certified that error appears in the above-identified patent and that said Letters Patent is hereby corrected as shown below:

Column 4,
Line 38, "qrs" should read -- QRS --
Line 44, "claim 2" should read -- claim 1 --
Line 46, "claim 1" should read -- claim 2 --
Line 63, "claim 5" should read -- claim 1 --

Column 6,
Line 25, "claim 23" should read -- claim 22 --
Line 28, "claim 24" should read -- claim 23 --
Line 36, "claim 24" should read -- claim 23 --

Signed and Sealed this

Eighth Day of October, 2002

*Attest:*

*Attesting Officer*

JAMES E. ROGAN
*Director of the United States Patent and Trademark Office*